(12) United States Patent
Zuccarelli et al.

(10) Patent No.: US 6,951,657 B1
(45) Date of Patent: Oct. 4, 2005

(54) PARTICLES COATED WITH GRANULATED CRYSTALLINE IBUPROFEN

(75) Inventors: Jean-Marc Zuccarelli, Antibes (FR); Charles André Chauveau, Valbonne (FR); Gilles DeMichelis, Grasse (FR); Karine Jean, Cagnes sur Mer (FR)

(73) Assignee: Laboratoires des produits Ethiques Ethypharm SA, Houdan (FR)

( * ) Notice: Subject to any disclaimer, the term of this patent is extended or adjusted under 35 U.S.C. 154(b) by 0 days.

(21) Appl. No.: 09/830,101

(22) PCT Filed: Nov. 3, 1999

(86) PCT No.: PCT/FR99/02682

§ 371 (c)(1),
(2), (4) Date: Mar. 5, 2002

(87) PCT Pub. No.: WO00/27368

PCT Pub. Date: May 18, 2000

(30) Foreign Application Priority Data

Nov. 6, 1998 (FR) .................................. 98 14033

(51) Int. Cl.⁷ .............................................. A61K 9/50
(52) U.S. Cl. ...................... 424/497; 424/490; 424/494; 424/495
(58) Field of Search ................................ 424/499, 489, 424/465, 441, 469

(56) References Cited

U.S. PATENT DOCUMENTS

| | | | |
|---|---|---|---|
| 4,308,251 A | * | 12/1981 | Dunn et al. ................ 424/19 |
| 4,588,612 A | | 5/1986 | Perkins et al. |
| 4,835,186 A | | 5/1989 | Reuter et al. |
| 4,835,187 A | * | 5/1989 | Reuter et al. ............... 514/570 |
| 5,084,278 A | | 1/1992 | Mehta |
| 5,191,114 A | * | 3/1993 | Chen .......................... 526/496 |
| 5,215,755 A | * | 6/1993 | Roche et al. ............... 424/480 |
| 5,275,824 A | * | 1/1994 | Carli et al. ................. 424/490 |
| 5,733,577 A | * | 3/1998 | Myers et al. ............... 424/488 |
| 5,814,332 A | * | 9/1998 | Ghanta et al. .............. 424/440 |

FOREIGN PATENT DOCUMENTS

| | | |
|---|---|---|
| GB | 2 178 313 | 2/1987 |
| WO | WO 91 15194 | 10/1991 |
| WO | WO 93 01805 | 2/1993 |

* cited by examiner

Primary Examiner—Thurman K. Page
Assistant Examiner—Micah-Paul Young
(74) Attorney, Agent, or Firm—Caesar, Rivise, Bernstein, Cohen & Pokotilow, Ltd.

(57) ABSTRACT

The invention concerns coated particles based on granulated microcrystals of ibuprofen, its pharmaceutically acceptable isomers and salts, characterized in that they comprise a coating obtained in a fluidized bed apparatus with a hydroalcoholic dispersion consisting of a mixture comprising (A) 5 to 50% by weight of ethylcellulose relative to ibuprofen; (B) 10 to 60% by weight of hydroxypeopylmethylcellulose relative to the ethylcellulose; and (C) 1 to 40% by weight of silica with antistatic and permeabilizing properties relative to the ethylcellulose, the resulting coating, whereof at least one of the constituents can be used for granulating the ibuprofen microcrystals resulting in said particles, thereby masking the unpleasant taste of ibuprofen and significantly reducing its irritating effect on the throat after deglutition and substantially immediate release of ibuprofen when the particles are placed in an aqueous medium.

9 Claims, No Drawings

PARTICLES COATED WITH GRANULATED CRYSTALLINE IBUPROFEN

The invention relates to coated particles based on granulated crystalline ibuprofen or its pharmaceutically acceptable salts or esters, which have a coating obtained in a fluidized bed apparatus with an aqueous-alcoholic dispersion, said coating masking the unpleasant taste of the ibuprofen, significantly reducing its irritant effect on the throat after swallowing, and releasing said ibuprofen substantially immediately when the particles reach the gastric medium.

It further relates to the process for the preparation of said particles.

The coated particles in question consist of granulated microcrystals of ibuprofen.

Patent U.S. Pat. No. 5,215,755 describes tablets in which the ibuprofen is present in the form of granules having a coating based on hydroxyethyl cellulose or a hydroxyethyl cellulose/hydroxypropyl methyl cellulose mixture. This coating affords a better compromise between taste masking and bioavailability, which could not be achieved by the use of ethyl cellulose on its own or mixed with other, already known coating polymers.

Patent U.S. Pat. No. 5,814,332 describes ibuprofen particles encapsulated by coacervation of the active principle with cellulosic polymers and gelatin.

Patents U.S. Pat. No. 4,835,186 and U.S. Pat. No. 4,835,187 describe ibuprofen powders obtained by a method in which suspensions of colloidal silica in solutions, in organic solvents, of ibuprofen and a cellulosic material such as ethyl cellulose, hydroxyethyl cellulose, hydroxypropyl methyl cellulose or cellulose acetophthalate are dried by atomization, said method is better known as nebulization.

The object of the invention is to provide novel particles based on crystalline ibuprofen which have a neutral palatability, are tasteless and mask the irritant effect of the active principle. Their particle size distribution and their physical characteristics enable them to be used especially in the manufacture of multiparticulate tablets disintegrating rapidly in the mouth under the action of the saliva, according to patent FR 2679451, and are such that the active principle is released substantially immediately.

As a result of in-depth researches, the Applicant succeeded in discovering that this object was achieved by using a process of granulation and coating in a fluidized bed apparatus with a mixture essentially based on ethyl cellulose, hydroxypropyl methyl cellulose and silica with antistatic and permeabilizing properties, in defined proportions.

Thus the particles according to the invention, based on granulated microcrystals of ibuprofen, its isomers and its pharmaceutically acceptable salts, are characterized in that they have a coating consisting of a mixture comprising A) from 5 to 50% by weight, preferably from 10 to 30% by weight, of ethyl cellulose, based on the ibuprofen, B) from 10 to 60% by weight, preferably from 15 to 50% by weight, of hydroxypropyl methyl cellulose, based on the ethyl cellulose, and C) from 0.1 to 40% by weight, preferably from 3 to 25% by weight, of silica with antistatic and permeabilizing properties, based on the ethyl cellulose, said coating—of which at least one of the constituents can be used for the granulation of the ibuprofen microcrystals to produce said particles—masking the unpleasant taste of the ibuprofen, significantly reducing its irritant effect on the throat after swallowing, and releasing the ibuprofen substantially immediately when the particles are placed in an aqueous medium.

The active principle consists of crystalline ibuprofen or one of its pharmaceutically acceptable salts or esters.

The active principle is commercially available in the form of microcrystals with a mean size of between 20 and 80 μm.

The disadvantage of this particle size is that coating by methods which consist in spraying a coating solution onto these microcrystals in a fluidized bed apparatus is difficult and lengthy.

According to the invention, to overcome this disadvantage, the ibuprofen microcrystals are granulated and coated to produce particles whose size is such that at least 80% of the particles are between 100 and 500 μm and less than 15% of the particles are smaller than 100 μm.

In the coated particles according to the invention, the ibuprofen preserves its physicochemical integrity, the intrinsic properties of the active principle being totally unchanged by granulation and coating.

The silica with antistatic and permeabilizing properties (C) can be selected from the group comprising especially colloidal silica, particularly the one marketed under the trade mark AEROSIL®, and preferably precipitated silica, particularly the one marketed under the trade mark SYLOID® FP244, and mixtures thereof.

Advantageously, it is also possible to use an agent (D) which directly or indirectly favours the solubilization of the ibuprofen, said agent being selected from the group comprising especially mannitol, starch, pharmaceutically acceptable self-emulsifying bases, polyvinylpyrrolidones, stearic macrogol glycerides, which are better known as gélucire, alkali metal salts of organic origin such as sodium bicarbonate, surfactants such as sodium laurylsulfate, and mixtures thereof. This agent (D) is present in proportions which can range up to 50% by weight, preferably up to 35% by weight, based on the ibuprofen.

In one advantageous embodiment, the ibuprofen particles are granulated with at least one agent favouring the solubilization of the ibuprofen, said agent preferably being selected from the group comprising stearic macrogol glycerides and hydroxypropyl methyl cellulose, and are coated with an ethyl cellulose/hydroxypropyl methyl cellulose mixture in proportions which make it possible to mask the taste and the irritant effect of the ibuprofen, and with a silica having antistatic and permeabilizing properties, especially precipitated silica, this embodiment optimizing the bioavailability of the ibuprofen.

This achieves a masking of the taste and the irritant effect which is just as satisfactory as with the other method of preparing the particles, but the rate of release of the active principle into aqueous media is optimized.

In another advantageous embodiment, the ibuprofen microcrystals are granulated in the presence of microcrystals of an alkali metal salt of organic origin as an agent favouring the solubilization of ibuprofen, and a solution comprising hydroxypropyl methyl cellulose and/or polyvinylpyrrolidone. This alkali metal salt is preferably sodium bicarbonate, which, by dissolving in the gastrointestinal fluids, creates an alkaline micro-pH favouring the solubilization of the ibuprofen particles.

The particles of this constitution are then coated with the coating mixture according to the invention.

In another advantageous embodiment, again in the case where at least one of the constituents of the coating is used for the granulation of the ibuprofen microcrystals, said coating contains an agent favouring solubilization, which can be a soluble agent such as mannitol or a swelling agent such as starch. If a soluble agent is used, it crystallizes on the surface of the ibuprofen particles and, in an acid medium, it solubilizes to leave pores which allow the physiological fluids to enter inside the particle. If a swelling agent is used, a complementary particle bursting phenomenon takes place.

The particles according to the invention optimize the dissolution of the ibuprofen in aqueous media. The rate of dissolution of the particles is such that, in a buffer solution of pH 7.2, 80% of the ibuprofen is released in 30 minutes and preferably in 15 minutes.

The invention further relates to a process for the preparation of coated particles based on ibuprofen microcrystals. This process comprises, simultaneously or successively, a phase consisting in granulating the ibuprofen microcrystals and a phase consisting in coating them with a coating made up of a mixture of A) 5 to 50% by weight, preferably 10 to 30% by weight, of ethyl cellulose, based on the ibuprofen, B) 10 to 60% by weight, preferably 15 to 50% by weight, of hydroxypropyl methyl cellulose, based on the ethyl cellulose, and C) 0.1 to 40% by weight, preferably 3 to 25% by weight, of silica with antistatic and permeabilizing properties, based on the ethyl cellulose;

at least one of the constituents of the mixture used for the coating can be used for the granulation of the ibuprofen microcrystals.

In the granulation and/or coating phases, it is also possible to use an agent (D) favouring the solubilization of the ibuprofen, said agent being selected from the group comprising mannitol, starch, pharmaceutically acceptable self-emulsifying bases, polyvinylpyrrolidones, stearic macrogol glycerides, alkali metal salts of organic origin, surfactants and mixtures thereof. In this case said agent (D) is present in proportions which can range up to 50% by weight, preferably up to 35% by weight, based on the ibuprofen.

The process according to the invention is carried out in a fluidized bed under temperature conditions such that the temperature of the ibuprofen is always kept below the melting and sublimation points of ibuprofen. In one particular embodiment of the process of the invention, the temperature of the ibuprofen is always kept below 45° C., preferably below 30° C.

Because the granulation and coating process used is carried out in a fluidized bed, the ibuprofen is not brought into solution, so it preserves its physicochemical integrity in optimal manner. Furthermore, the use of low temperatures enables any change of state and any risk of degradation of the active principle to be avoided.

In a first embodiment, the granulation and coating phases take place simultaneously by wetting the ibuprofen microcrystals with an aqueous-alcoholic suspension comprising especially ethyl cellulose and hydroxypropyl methyl cellulose and a silica with antistatic and permeabilizing properties.

In another embodiment of the process according to the invention, the first step, or granulation phase, is carried out using at least one agent favouring solubilization, selected from the group comprising especially stearic macrogol glycerides and hydroxypropyl methyl cellulose, and the second step, or coating phase, is then carried out using a silica with antistatic and permeabilizing properties and a mixture of ethyl cellulose and hydroxypropyl methyl cellulose in proportions which make it possible to mask the taste and the irritant effect of the ibuprofen and to release the ibuprofen substantially immediately.

In another advantageous embodiment of the process according to the invention, in the first step, or granulation step, ibuprofen microparticles are mixed with microcrystals of an alkali metal salt of organic origin as an agent favouring the solubilization of the ibuprofen, and the resulting mixture is granulated with an aqueous-alcoholic dispersion comprising hydroxypropyl methyl cellulose and/or polyvinylpyrrolidone. The coating phase is then carried out with a coating mixture according to the invention.

EXAMPLES

Preparation of Coated Ibuprofen Granules

Example 1

The unit formulation of the coated granules is as follows:

| | |
|---|---|
| Ibuprofen | 200.00 |
| Ethyl cellulose N7 | 40.00 |
| Colloidal silica | 3.00 |
| Hydroxypropyl methyl cellulose | 8.00 |
| | 251.00 mg |

These granules are prepared by the following procedure:

The first step is to prepare a coating dispersion by introducing 24 g of hydroxypropyl methyl cellulose into 390 g of purified water and stirring until the hydroxypropyl methyl cellulose has completely dissolved. In a separate operation, 9 g of colloidal silica and 120 g of ethyl cellulose N7 are introduced into 110 g of alcohol and the mixture is stirred until a homogeneous dispersion is obtained.

The solution and dispersion obtained above are then mixed, stirring being maintained in order to prevent any sedimentation. A coating dispersion is thus obtained.

The second step is to prepare the coated granules by introducing 600 g of ibuprofen into the cell of a GLATT GPCG1 fluidized bed apparatus and fluidizing the ibuprofen under conditions such that its temperature is kept between 20 and 40° C. The previously prepared coating dispersion is then sprayed onto the bed of ibuprofen obtained above in such a way that the temperature of the product is kept between 15 and 30° C.

50% of the coating dispersion is sprayed for about 1 hour and this is followed by drying for 2 to 5 minutes. The granules obtained are graded on a screen of aperture size 400 $\mu$m. The graded granules are then coated with the remaining coating dispersion for approximately 1 h 30 minutes, after which the coated granules are dried for about 5 minutes.

The coated granules contain 79.7% by weight of ibuprofen.

Using a type 4 apparatus described in USP XXIII page 1794, the kinetics of dissolution of the resulting granules are measured in a buffer medium of pH 7.2 with a dissolution volume of 900 ml. The results obtained are indicated below:

| Dissolution time in min | Ibuprofen dissolved in % |
|---|---|
| 15 | 88.1 |
| 30 | 100 |

Example 2

The unit formulation of the coated granules is as follows:

| | |
|---|---|
| Ibuprofen | 200.00 mg |
| Ethyl cellulose N7 | 40.00 mg |
| Hydroxypropyl methyl cellulose (HPMC) | 8.00 mg |
| Precipitated silica (Syloid ® FP244) | 13.70 mg |
| | 261.70 mg |

These granules are prepared by the following procedure:

The first step is to prepare a coating dispersion by introducing 24 g of HPMC into 459 g of purified water and stirring until the HPMC has completely dissolved. In a separate operation, 41.9 g of precipitated silica, marketed under the name Syloid® FP244, and 120 g of ethyl cellulose N7 are introduced into 1362 g of alcohol and the mixture is stirred until a homogeneous dispersion is obtained.

The solution and dispersion obtained above are then mixed, stirring being maintained in order to prevent any sedimentation. A coating dispersion is thus obtained.

The second step is to prepare the coated granules by introducing 600 g of ibuprofen into the cell of a Glatt GPCG1 fluidized bed apparatus and fluidizing the ibuprofen under conditions such that its temperature is kept between 20° C. and 40° C. The previously prepared coating dispersion is then sprayed onto the bed of ibuprofen obtained above in such a way that the temperature of the product is kept between 15° C. and 30° C.

50% of the coating dispersion is sprayed for about 1 hour and this is followed by drying for 2 to 5 minutes. The granules obtained are graded on a screen of aperture size 400 μm. The graded granules are then coated with the remaining coating dispersion for approximately one hour thirty minutes, after which the coated granules are dried for about 5 minutes.

The coated granules obtained contain 76.4% by weight of ibuprofen.

Example 3

The unit formulation of the coated granules is as follows:

| | |
|---|---|
| Ibuprofen | 200.00 mg |
| Sodium bicarbonate | 81.70 mg |
| Ethyl cellulose | 59.90 mg |
| HPMC | 28.60 mg |
| Colloidal silica | 5.50 mg |
| | 375.70 mg |

Preparation of the Granules:

The first step is to prepare a granulating dispersion by dissolving 50 g of HPMC in 600 ml of purified water and then adding 3 g of colloidal silica, stirring being maintained in order to prevent any sedimentation.

The second step is to prepare the granules by introducing 600 g of ibuprofen and 245 g of sodium bicarbonate into the cell of a Glatt GPCG1 fluidized bed apparatus and fluidizing the mixture of powders under conditions such that its temperature is kept between 20° C. and 40° C. The previously prepared granulating dispersion is then sprayed onto the bed of powders obtained above in such a way that the temperature of the product is kept between 15° C. and 30° C.

The granulating dispersion is sprayed for about 1 hour 30 minutes and this is followed by drying for 2 to 5 minutes. The granules obtained are graded on a screen of aperture size 500 μm.

Preparation of the Coated Granules:

These granules are prepared by the following procedure:

The first step is to prepare a coating dispersion by introducing 24 g of HPMC into 390 g of purified water and stirring until the HPMC has completely dissolved. In a separate operation, 9 g of colloidal silica and 120 g of ethyl cellulose N7 are introduced into 1160 g of alcohol and the mixture is stirred until a homogeneous dispersion is obtained.

The solution and dispersion obtained above are then mixed, stirring being maintained in order to prevent any sedimentation. A coating dispersion is thus obtained.

The second step is to prepare the coated granules by introducing 600 g of ibuprofen granules prepared in the previous step into the cell of a Glatt GPCG1 fluidized bed apparatus and fluidizing the granules under conditions such that their temperature is kept between 20° C. and 40° C.

The previously prepared coating dispersion is then sprayed onto the granules in such a way that the temperature of the product is kept between 15° C. and 30° C.

50% of the coating dispersion is sprayed for about 1 hour and this is followed by drying for 2 to 5 minutes. The granules obtained are graded on a screen of aperture size 500 μm. The graded granules are then coated with the remaining coating dispersion for approximately one hour, after which the coated granules are dried for about 5 minutes.

The coated granules obtained contain 53.1% by weight of ibuprofen.

Example 4

The unit formulation of the coated granules is as follows:

| | |
|---|---|
| Ibuprofen | 200.00 mg |
| Corn starch | 75.00 mg |
| Ethyl cellulose | 50.00 mg |
| HPMC | 10.00 mg |
| Colloidal silica | 3.50 mg |
| | 338.50 mg |

Preparation of the Granules:

The granules are prepared by the following procedure:

600 g of ibuprofen and 150 g of corn starch are introduced into a Lödige bag-type mixer-granulator and granulated with 550 g of purified water. The granules obtained are dried in an oven and then graded on a screen of aperture size 500 μm.

Preparation of the Coated Granules:

These coated granules are prepared by the following procedure:

The first step is to prepare a coating dispersion containing HPMC and corn starch by introducing 20 g of HPMC into 333 g of purified water, then stirring until the HPMC has completely dissolved, then adding 50 g of corn starch and stirring the mixture until a homogeneous dispersion is obtained.

In a separate operation, 3.5 g of colloidal silica and 100 g of ethyl cellulose N7 are introduced into 833 g of alcohol and the mixture is stirred until a homogeneous dispersion is obtained.

The two dispersions obtained above are then mixed, stirring being maintained in order to prevent any sedimentation. A coating dispersion is thus obtained.

The second step is to prepare the coated granules by introducing 500 g of ibuprofen granules prepared in the previous step into the cell of a Glatt GPCG1 fluidized bed apparatus and fluidizing the granules under conditions such that their temperature is kept between 20° C. and 40° C.

The previously prepared coating dispersion is then sprayed onto the granules in such a way that the temperature of the product is kept between 15° C. and 30° C.

50% of the coating dispersion is sprayed for about 1 hour and this is followed by drying for 2 to 5 minutes. The granules obtained are graded on a screen of aperture size 500 $\mu$m. The graded granules are then coated with the remaining coating dispersion for approximately one hour, after which the coated granules are dried for about 5 minutes.

The coated granules obtained contain 59.1% by weight of ibuprofen.

What is claimed is:

1. Coated particles based on granulated microcrystals of ibuprofen, its isomers and its pharmaceutically acceptable salts, wherein they have a coating consisting of a mixture consisting of:
   A) from 5 to 50% by weight, of ethyl cellulose, based on the ibuprofen,
   B) from 10 to 60% by weight, of hydroxypropyl methyl cellulose, based on the ethyl cellulose,
   C) from 0.1 to 40% by weight, of silica with antistatic and permeabilizing properties, based on the ethyl cellulose, and
   D) from 0 to 50% by weight of an agent favoring the solubilization of the ibuprofen, based on the ibuprofen, said agent being selected from the group comprising mannitol, starch, pharmaceutically acceptable self-emulsifying bases, polyvinylpyrrolidones, stearic macrogol glycerides, alkali metal salts of organic origin, surfactants and mixtures thereof,
whereby said coating—of which at least one of the constituents can be used for the granulation of the ibuprofen microcrystals to produce said particles—allows the masking of the unpleasant taste of the ibuprofen, the significantly reduction of its irritant effect on the throat after swallowing, and the release of 80% of the ibuprofen in 30 minutes in 900 ml of a buffer solution of pH 7.2, using a type 4 apparatus described in USP XXIII p. 1794.

2. Particles according to claim 1, having a coating consisting of a mixture consisting of
   A) from 10 to 30% by weight, of ethyl cellulose, based on the ibuprofen,
   B) from 15 to 50% by weight, of hydroxypropyl methyl cellulose, based on the ethyl cellulose,
   C) from 3 to 25% by weight, of silica with antistatic and permeabilizing properties, based on the ethyl cellulose, and
   D) from 0 to 35% by weight of an agent favoring the solubilization of the ibuprofen, based on the ibuprofen.

3. Particles according to claim 1, wherein the silica with antistatic and permeabilizing properties (C) is precipitated silica.

4. Particles according to claim 1, wherein the size distribution of the particles is such that at least 80% of the particles are between 100 and 500 $\mu$m and less than 15% of the particles are smaller than 100 $\mu$m.

5. Particles according to claim 1, wherein in a buffer solution of pH 7.2, 80% of the ibuprofen is released in 15 minutes.

6. Process for the preparation of coated particles based on granulated microcrystals of ibuprofen, its isomers and its pharmaceutically acceptable salts, wherein it comprises, successively, phases consisting in granulating the ibuprofen microcrystals and coating them with a mixture consisting of:
   A) 5 to 50% by weight, of ethyl cellulose, based on the ibuprofen,
   B) 10 to 60% by weight, of hydroxypropyl methyl cellulose, based on the ethyl cellulose, and
   C) 0.1 to 40% by weight, of silica with antistatic and permeabilizing properties, based on the ethyl cellulose; and
   D) 0 to 50% by weight based on ibuprofen or an agent favouring the solubilization of the ibuprofen, said agent being selected from the group comprising mannitol, starch, pharmaceutically acceptable self-emulsifying bases, polyvinylpyrrolidones, stearic macrogol glycerides, alkali metal salts of organic origin, surfactants and mixtures thereof, at least one of the constituents of the mixture used for the coating can be used for the granulation of the ibuprofen microcrystals.

7. Process according to claim 6, wherein the mixture consists of:
   A) 10 to 30% by weight of ethyl cellulose, based on the ibuprofen,
   B) 15 to 50% by weight of hydroxypropyl methyl cellulose, based on the ethyl cellulose,
   C) 3 to 25% by weight of silica with antistatic and permeabilizing properties, based on the ethyl cellulose; and
   D) 0 to 35% by weight based on ibuprofen of the agent favouring the solubilization of the ibuprofen.

8. Process according to claim 6, wherein it is carried out in a fluidized bed apparatus with an aqueous-alcoholic dispersion under conditions such that the temperature of the ibuprofen is always below 45° C.

9. Process according to claim 8, wherein it is carried out in a fluidized bed apparatus with an aqueous-alcoholic dispersion under conditions such that the temperature of the ibuprofen is always below 30° C.

* * * * *